United States Patent
Bissah et al.

(10) Patent No.: US 6,565,547 B2
(45) Date of Patent: May 20, 2003

(54) BUNCHING RESISTANT ASSORBENT ARTICLE

(75) Inventors: Kofi Ayensu Bissah, Somerset, NJ (US); Michelle Renee Corley, West Windsor, NJ (US); Jutta S. Haarer, Lawrenceville, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/348,956

(22) Filed: Jul. 7, 1999

(65) Prior Publication Data

US 2001/0051795 A1 Dec. 13, 2001

(51) Int. Cl.⁷ ................................................ A61F 13/15
(52) U.S. Cl. ................................ 604/385.01; 604/378
(58) Field of Search ........................... 604/385.23, 386, 604/385.31, 387, 397, 385.01, 378

(56) References Cited

U.S. PATENT DOCUMENTS

| 4,886,513 A | | 12/1989 | Mason, Jr. et al. | |
| 4,963,139 A | * | 10/1990 | Dabroski | 604/378 |
| 4,973,325 A | | 11/1990 | Sherrod et al. | |
| 5,098,422 A | | 3/1992 | Davis et al. | |
| 5,248,309 A | * | 9/1993 | Serbiak et al. | 604/368 |
| 5,383,869 A | | 1/1995 | Osborn, III | |
| 5,387,208 A | | 2/1995 | Ashton et al. | |
| 5,423,787 A | | 6/1995 | Kjellberg | |
| 5,575,786 A | | 11/1996 | Osborn, III | |
| 5,591,150 A | | 1/1997 | Olsen et al. | |
| 5,607,415 A | | 3/1997 | Datta et al. | |
| 5,609,588 A | | 3/1997 | DiPalma et al. | |
| 5,613,961 A | * | 3/1997 | DiPalma et al. | 604/369 |
| 5,649,916 A | | 7/1997 | DiPalma et al. | |
| 5,722,967 A | | 3/1998 | Coles | |
| 5,803,920 A | | 9/1998 | Gilman | |
| 5,833,678 A | | 11/1998 | Ashton et al. | |
| 5,868,727 A | | 2/1999 | Barr et al. | |
| 5,916,670 A | * | 6/1999 | Tan et al. | 428/219 |
| 6,210,385 B1 | * | 4/2001 | Mizutani | 604/385.01 |

FOREIGN PATENT DOCUMENTS

| EP | 172 035 A2 | 2/1986 |
| EP | 442 223 A1 | 8/1991 |
| FR | 2 513 115 | 3/1983 |
| GB | 2 170 108 A | 7/1986 |
| GB | 2 319 187 A | 5/1998 |
| HU | 217 377 B | 7/1993 |
| WO | WO 93/21879 A1 | 11/1993 |
| WO | 99/09925 | 4/1999 |

OTHER PUBLICATIONS

Copy of European Search Report Dated Jun. 27, 2001.
Hungarian Novelty Search Report (Application No. P 00 02592).

* cited by examiner

*Primary Examiner*—Dennis Ruhl

(57) ABSTRACT

An absorbent article is provided having excellent resistance to bunching. The absorbent article exhibits a Bunching Resistance in the range of about 205 g to 450 g and may be formed with an absorbent core comprising at least two absorbent layers having different Gurley Stiffnesses.

2 Claims, 2 Drawing Sheets

BUNCHING RESISTANT ASSORBENT ARTICLE

The present invention relates to an absorbent article having excellent resistance to bunching. The absorbent article exhibits a Bunching Resistance in the range of about 205 g to about 450 g and may be formed with an absorbent core comprising at least two absorbent layers having different Gurley Stiffnesses.

BACKGROUND OF THE INVENTION

An absorbent article such as a sanitary napkin, pantiliner, diaper, incontinence pad, or interlabial article typically comprises a liquid permeable cover on its body facing side, a barrier on its garment facing side, and an absorbent core in between. A common problem with absorbent articles is bunching and deformation of the article due to movement of the person wearing it. Bunching and deformation in turn impair the ability of the article to absorb exudates from the body.

Several suggestions for solving the problem of bunching have been made. For example, U.S. Pat. No. 4,886,513 to Mason, Jr. et al. discloses a pad comprising a flexibly stiff reinforcing member to maintain the pad's shape. The reinforcing member may be for example a strip of polyethylene extending around the periphery of the pad.

U.S. Pat. Nos. 5,609,588 to DiPalma et al. and 5,803,920 to Gilman et al. relate to the use of a resilient layer of non-absorbent foam in a sanitary napkin. The resilient layer is said to resist bunching during use of the napkin, so that the napkin has reduced twisting and bunching.

U.S. Pat. No. 5,387,208 to Ashton et al. discloses an absorbent article with an absorbent core having improved integrity by virtue of the presence of a primary core integrity layer. The primary core integrity layer is made of a liquid impervious mesh of thermoplastic material, preferably a hot melt adhesive.

U.S. Pat. No. 4,973,325 to Sherrod et al. relates to an absorbent article having a transfer member positioned between two side-by-side absorbents. The transfer member is said to allow the absorbent article to flex in the middle and conform to the body of the wearer, thereby reducing bunching.

U.S. Pat. No. 5,575,786 to Osborn recites in claim 1 a sanitary napkin comprising absorbent portions aligned along the longitudinal centerline of the napkin and peripheral portions aligned adjacent to the absorbent portions. The peripheral portions have a different stiffness than the absorbent portions, and the difference in stiffness is claimed to substantially prevent bunching of the napkin when the napkin is subjected to lateral stresses.

Despite these attempts at maintaining the physical integrity of absorbent articles, an absorbent article having even better anti-bunching properties is needed. Applicants have identified a class of such absorbent articles. Specifically, the present invention provides an absorbent article, such as a sanitary napkin, pantiliner, diaper, incontinence pad, or an interlabial article, in particular a thin absorbent article, comprising in sequence a liquid permeable cover, an absorbent core, and a barrier, having a caliper of less than 0.2 inches, a length of less than about 8 inches, a width of less than about 4 inches, and a Bunching Resistance of at least about 205 g. Preferably, the absorbent article comprises an absorbent core comprising at least two absorbent layers having different Gurley Stiffnesses.

SUMMARY OF THE INVENTION

The present invention provides an absorbent article comprising in sequence a liquid permeable cover, an absorbent core, and a barrier, wherein the absorbent article has a caliper of less than about 0.2 inches, a length of less than about 8 inches, a width of less than about 4 inches, and exhibits a Bunching Resistance of about 205 g to about 450 g.

The present invention further provides an absorbent article comprising in sequence a liquid permeable cover, an absorbent core comprising at least two absorbent layers having different Gurley Stiffnesses, and a barrier.

DETAILED DESCRIPTION OF THE INVENTION

The absorbent article may for example be a sanitary napkin, a pantiliner, a diaper, incontinence pad, interlabial article, or other similar product for absorbing exudates from the body, such as menses, urine, and feces. Preferably, the absorbent article is a sanitary napkin or a pantiliner. Such sanitary napkin or pantiliner may have an approximately rectangular, oval, dogbone, or peanut shape. The absorbent article is thin, i.e., having a caliper of less than about 5 mm. Preferably, the caliper of the absorbent article is less than about 3 mm, more preferably less than about 2.5 mm. The absorbent article has a length of less than about 8 inches, preferably 7 inches, and a width of less than about 4 inches, preferably less than about 3 inches.

Figure 1:
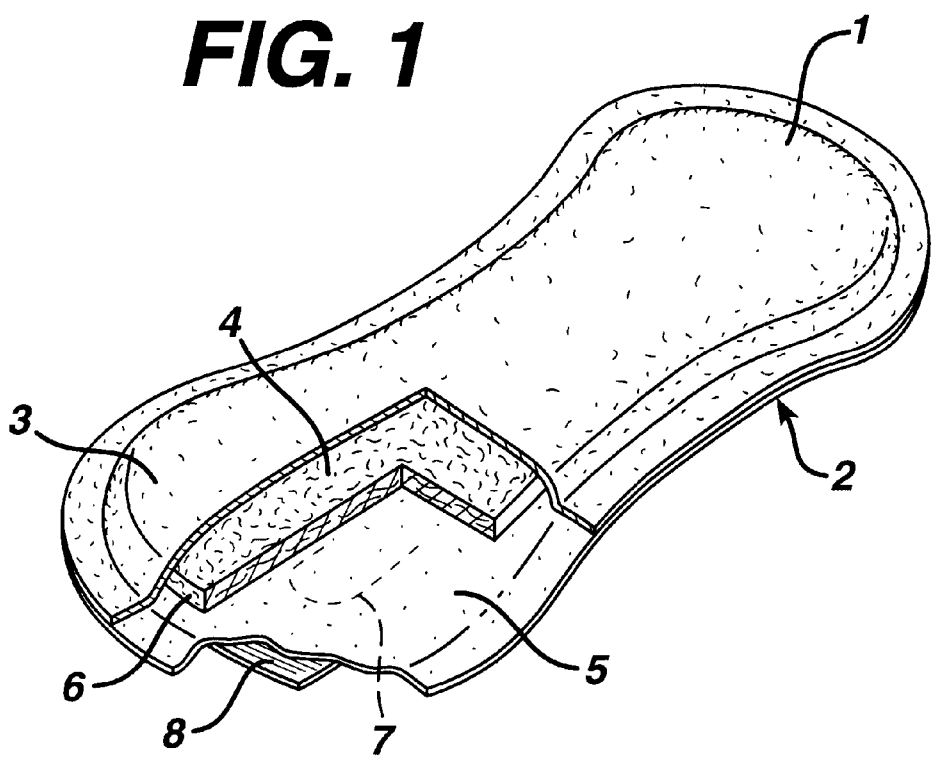
FIG. 1 is a perspective view of a pantiliner according to the invention.

FIG. 1 depicts a pantiliner according to the invention, and is used for purposes of illustration in the following description of the invention. The pantiliner shown in FIG. 1 comprises in sequence from its body-facing side 1 to its garment-facing side 2 a liquid permeable cover 3, an absorbent core 4, and a barrier 5. The liquid permeable cover 3 of the absorbent article may be formed from any fluid pervious material that is comfortable against the skin and that permits fluid to penetrate to the absorbent core, which retains the fluid. A variety of materials are known for this purpose, and any of these may be used. The cover should retain little or no fluid in its structure to provide a relatively dry surface next to the skin. The cover may be a fibrous non-woven fabric made of fibers or filaments of polymers such as polyethylene, polypropylene, polyester, or cellulose. Alternatively, the cover may be formed from an apertured polymeric film. The thickness of the cover may vary from approximately 0.001 to 0.062 inch, depending on the material chosen. Generally, the liquid permeable cover 3 is a single sheet of material having a width sufficient to cover the body-facing side 1 of the article.

The absorbent article further comprises a barrier 5 on its garment facing side 2. The barrier is typically liquid impermeable and may comprise any thin, flexible, material such as a polymeric film, for example, polyethylene, polypropylene, or cellophane. Alternatively, the barrier may be a normally fluid permeable material that has been treated to be impermeable, such as impregnated fluid repellent paper or non-woven fabric material, or a flexible foam, such as polyurethane or cross-linked polyethylene. If higher Bunching Resistance is desired, a foam, particularly a closed cell foam, may be used as the barrier. The barrier may be a single or multilayer structure, and may also be "breathable," that is liquid impermeable and vapor permeable. The thickness of the barrier when formed from a polymeric film typically is about 0.0005 to 0.002 inch. A variety of materials are known in the art for use as barriers, and any of these may be used.

Generally, the barrier 5 has a width sufficient to cover the garment-facing side 2 of the absorbent article. The barrier may extend around the sides of the absorbent core in a C-shaped configuration with the portions of the barrier that are adjacent its longitudinal edges extending upwardly from the garment facing side toward the body facing side of the article.

The absorbent core 4 comprises at least one absorbent layer 6. In a preferred embodiment of the invention, the absorbent core comprises at least two absorbent layers having different Gurley Stiffnesses. Gurley Stiffness is measured by TAPPI T543 om-94.

For example, the absorbent core may comprise two absorbent layers, one having a high Gurley Stiffness, i.e., greater than about 100, preferably greater than about 120, more preferably greater than about 150, milligrams, and one having a low Gurley Stiffness, i.e., less than about 50, preferably less than about 40, more preferably less than about 35, milligrams. When two absorbent layers are employed, the first absorbent layer proximal the liquid permeable cover has a low Gurley Stiffness, i.e., less than about 50 milligrams, and the second absorbent layer proximal the barrier has a high Gurley Stiffness, i.e., greater than about 100 milligrams.

Alternatively, the absorbent core may comprise three absorbent layers with alternating Gurley Stiffnesses: high/low/high or low/high/low. Similarly, the absorbent core may comprise four or more absorbent layers with alternating high and low Gurley Stiffnesses, as desired.

In another embodiment, the absorbent core comprises a single absorbent layer having zones with different Gurley Stiffnesses. Such zones may result in Gurley Stiffness variations along the length, width, or thickness, or combinations of these, of the absorbent layer.

Construction of an absorbent core comprising absorbent layers of differing Gurley Stiffnesses advantageously provides the absorbent article with stiffness and flexibility simultaneously. The high Gurley Stiffness layer provides rigidity and stability, while the low Gurley Stiffness layer provides flexibility and suppleness. The total effect of this combined structure results in an absorbent article having superior anti-bunching properties as well as flexibility.

One particularly useful absorbent core comprises two absorbent layers of thermobond airlaid fibrous web with one or more superabsorbent polymers in between. The first absorbent layer proximal the body facing side of the article comprises about 50 to 65% pulp, the remainder being a combination of polyethylene/polypropylene bicomponent fibers and polyethylene/polyester bicomponent fibers, and has a Gurley Stiffness in the range of about 20 to about 50, preferably about 25 to about 35, milligrams. The second absorbent layer proximal the garment facing side of the article comprises less than about 50% pulp, the remainder being a combination of polyethylene/polypropylene bicomponent fibers and polyethylene/polyester bicomponent fibers, and has a Gurley Stiffness of about 100 to about 200, preferably about 135 to about 175, milligrams.

The absorbent article may be applied to the crotch of underpants by placing the garment facing side of the absorbent article against the inside surface of the crotch of the underpants. Strips of pressure sensitive adhesive 7 may be applied to the garment facing side 2 of the absorbent article to help maintain it in place. As used herein, the term "pressure-sensitive adhesive" refers to any releasable adhesive or releasable tenacious means. Suitable pressure sensitive adhesives include for example water-based adhesives such as acrylate adhesives. Alternatively, the adhesive may comprise rapid setting thermoplastic "hot melt" rubber adhesives or two-sided adhesive tape.

A paper release strip 8 that has been coated on one side, may be applied to protect the strips of adhesive 7 prior to use. The coating, for example silicone, reduces adherence of the coated side of the release strip to the adhesive. The release strip can be formed from any suitable sheet-like material which, when coated, adheres with sufficient tenacity to the adhesive to remain in place prior to use but can be readily removed when the absorbent article is to be used.

The absorbent article may comprise other known materials and layers, such as transfer layers, foam layers, odor control agents, construction adhesives, all of which are known in the art. The absorbent article can optionally be embossed with decorative designs using conventional techniques.

The absorbent core may optionally contain superabsorbent polymers, either in one of more absorbent layers, or preferably in between the absorbent layers. Superabsorbent polymers are used to increase the liquid management properties of absorbent articles, such as capacity and retention of fluids. The amount of superabsorbent polymer contained by the absorbent article may range from about 0.1 to about 5 grams, preferably from about 0.2 to about 2.5 grams, more preferably from about 0.3 to about 1 grams.

Figure 2:
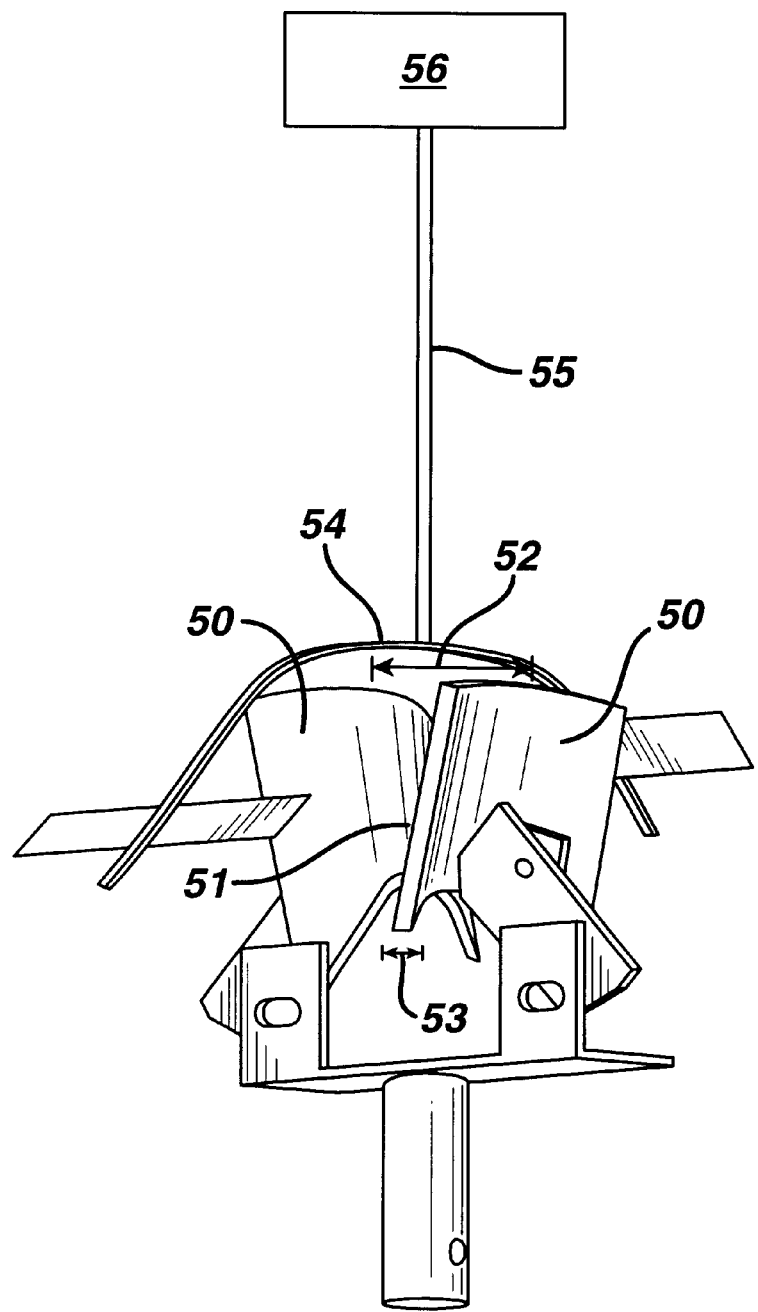
FIG. 2 depicts the apparatus used for the Curved Longitudinal Bending Test.

The absorbent article has a Bunching Resistance of about 205 to about 450 g, preferably about 250 to about 360 g. Bunching Resistance is measured by the Curved Longitudinal Bending Test, which is carried out on an anatomically shaped apparatus as shown in FIG. 2. The apparatus comprises two smooth, convex, stainless steel plates 50 placed at a 40 degree angle from one another to form a v-shaped trough 51. The widest distance (at the top) between the plates 52 is 73 mm and the narrowest distance (at the bottom) 53 is 18 mm. A vertically movable, curved pad holder 54 is supported by a shaft 55 and centered between the plates 50. The shaft 55 is connected to a tensionmeter 56. The holder 54 is placed perpendicular to the horizontal axis of the two plates 50. The tensionmeter 56 measures the compression force needed to deform a sample lengthwise in the narrow gap 53 of 18 mm. The tensionmeter is initially set at 50 kg. The shaft speed is set at 50.0 centimeters per minute per full stroke length. Any release paper is removed from the absorbent article prior to placement in the apparatus, and talc powder is applied to exposed positioning adhesive to provide a tackless surface. The article is placed, with cover facing down and the barrier facing up, in the holder 54, and the shaft 55 is actuated. The peak loads are measured for 5 cycles. Values are reported as peak Load 1, peak load 5, and % drop between load 1 and load 5.

The Bunching Resistance of the present absorbent article is very high, higher than that of known absorbent articles of similar thickness. The low level of bunching experienced with these products provides a more comfortable body facing surface against the skin and avoids the formation of channels that encourage the fluid to flow laterally out of the absorbent article.

The following non-limiting examples further illustrate the invention.

EXAMPLES 1–15 AND A–II

A series of pantiliners having thicknesses in the range of 0.06 to 0.2 inches were subjected to the Curved Longitudinal Bending Test using the apparatus shown in FIG. 2. Examples A–II were commercially available pantiliners, while Examples 1–15 were pantiliners of the invention.

Specifically, the pantiliners of Examples 1–15 comprised a liquid permeable cover, an absorbent core comprising two absorbent layers, and a barrier. The absorbent layer adjacent the liquid permeable cover was made of about 50 to 65% pulp, the remainder being a combination of polyethylene/polypropylene bicomponent fibers and polyethylene/polyester bicomponent fibers. The absorbent layer adjacent the barrier was made of less than about 50% pulp, the remainder being a combination of polyethylene/polypropylene bicomponent fibers and polyethylene/polyester bicomponent fibers. It should be noted that the pantiliners of Examples 6–10 were handmade samples.

The results are given in the Tables.

TABLE 1

Invention

| Example | Bend Resistance [g] |
|---------|---------------------|
| 1 | 298.1 |
| 2 | 293 |
| 3 | 296.1 |
| 4 | 246.4 |
| 5 | 271 |
| Mean: | 280.92 |
| 6 | 186 |
| 7 | 165.1 |
| 8 | 175.6 |
| 9 | 183.3 |
| 10 | 166.8 |
| Mean: | 175.36 |
| 11 | 259.3 |
| 12 | 238.4 |
| 13 | 243.4 |
| 14 | 261.5 |
| 15 | 231 |
| Mean: | 246.72 |

TABLE 2

ALWAYS ALLDAYS*

| Example | Bend Resistance [g] |
|---------|---------------------|
| A | 198.4 |
| B | 196.3 |
| C | 173.9 |
| D | 170.5 |
| E | 201.4 |
| Mean: | 188.1 |

TABLE 3

ALLDAYS Light*

| Example | Bend Resistance [g] |
|---------|---------------------|
| F | 197.2 |
| G | 192.1 |
| H | 190.9 |
| I | 204 |
| J | 192 |
| Mean: | 195.24 |

TABLE 4

KOTEX Lightdays**

| Example | Bend Resistance [g] |
|---------|---------------------|
| K | 102.0 |
| L | 104.7 |
| M | 98.9 |
| N | 101.9 |
| O | 82.1 |
| P | 75.4 |
| Q | 85.1 |
| R | 94.3 |
| S | 88.1 |
| T | 101.5 |
| Mean: | 93.4 |

TABLE 5

CAREFREE To Go***

| Example | Bend Resistance [g] |
|---------|---------------------|
| U | 55.1 |
| V | 49.3 |
| W | 39.5 |
| X | 45.7 |
| Y | 39.2 |
| Z | 49.3 |
| AA | 46.3 |
| BB | 53.1 |
| CC | 36.8 |
| DD | 41.4 |
| EE | 43.2 |
| FF | 44.3 |
| GG | 48.9 |
| HH | 38.8 |
| II | 42.1 |
| Mean: | 44.9 |

*Commercially available from Procter & Gamble Company.
**Commercially available from Kimberly Clark Corp.
***Commercially available from Personal Products Worldwide, a division of McNeil-PPC, Inc.

EXAMPLES 16–35

Ten, two layer absorbent cores of the same type used in the pantiliners of Examples 1–15 were tested for Gurley Stiffness as follows. In each case, the two absorbent layers were separated from each other, and the Gurley Stiffness of each layer was measured according to by TAPPI T543 om-94. The results are shown in Tables 6 and 7. Examples 16–25 were the absorbent layers proximal the covers of the pantiliners (5 g weight in the 2 inch position, factor 11.1). Examples 26–35 were the absorbent layers proximal the barriers of the pantiliners (25 g weight in the 2 inch position, factor 55.6).

TABLE 6

Gurley Stiffness

| Example | Milligrams |
|---------|------------|
| 16 | 36.075 |
| 17 | 24.975 |
| 18 | 31.635 |
| 19 | 30.525 |
| 20 | 28.86 |
| 21 | 35.52 |
| 22 | 40.515 |
| 23 | 25.53 |

TABLE 6-continued

Gurley Stiffness

| Example | Milligrams |
|---|---|
| 24 | 27.195 |
| 25 | 30.525 |
| Average | 31.14 |

TABLE 7

Gurley Stiffness

| Example | Milligrams |
|---|---|
| 26 | 155.68 |
| 27 | 183.48 |
| 28 | 155.68 |
| 29 | 169.58 |
| 30 | 144.56 |
| 31 | 177.92 |
| 32 | 183.48 |
| 33 | 150.12 |
| 34 | 177.92 |
| 35 | 166.8 |
| Average | 166.52 |

EXAMPLE 37

Several commercially available pantiliners and two having the same construction as the pantiliners of Examples 1–15 were tested for comfort with groups of consumers. The consumers were asked to use the pantiliners and rate them on a scale of 1 to 10 for comfort to wear. The results are given in Table 8.

TABLE 8

Comfort

| Product | Average Rating for Comfort to Wear (0–10) | Number of Women |
|---|---|---|
| Kao* | 7.5 | 104 |
| KOTEX Lightdays** | 7.6 | 140 |
| ALLDAYS Light*** | 8 | 153 |
| Invention | 8.5 | 140 |
| ALWAYS Alldays*** | 7.7 | 140 |
| Invention | 8 | 140 |

*Commerically available from Kao Corp.
**Commercially available from Kimberley Clark Corp.
***Commercially available from Procter & Gamble Company.

We claim:

1. An absorbent article comprising in sequence a liquid permeable cover, an absorbent core, and a barrier, wherein the absorbent core comprises at least two absorbent layers having different Gurley Stiffnesses, wherein a first absorbent layer proximal the liquid permeable cover has a Gurley Stiffness of less than 50 milligrams and a second absorbent layer proximal the barrier has a Gurley Stiffness of greater than about 120 milligrams and wherein the absorbent article has a caliper of less than about 0.2 inches, a length of less than 8 inches, a width of less than 4 inches, and exhibits a Bunching Resistance of about 205 g. to about 450 g.

2. An absorbent article comprising in sequence a liquid permeable cover, an absorbent core comprises at least two absorbent layers having different Gurley Stiffnesses comprises three absorbent layers in sequence, wherein the first and third layers sandwich the second layer and have substantially the same Gurley Stiffness, while the second layer has a different Gurley Stiffness, and a barrier, wherein the absorbent article has a caliper of less than about 0.2 inches, a length of less than about 8 inches, a width of less than about 4 inches, and exhibits a Bunching Resistance of about 205 g. to about 450 g.

* * * * *